United States Patent
Ohsaki et al.

[11] Patent Number: 5,477,318
[45] Date of Patent: Dec. 19, 1995

[54] APPARATUS FOR DETECTING A PROPERTY OF A LIQUID

[75] Inventors: Rie Ohsaki, Anjo; Masayuki Goto, Kariya; Yasuyoshi Toda, Anjo, all of Japan

[73] Assignee: Nippondenso Co., Ltd., Kariya, Japan

[21] Appl. No.: 418,889

[22] Filed: Apr. 7, 1995

Related U.S. Application Data

[63] Continuation of Ser. No. 120,378, Sep. 14, 1993, abandoned.

[30] Foreign Application Priority Data

Sep. 16, 1992 [JP] Japan ................................. 4-272420
Aug. 4, 1993 [JP] Japan ................................. 5-213444

[51] Int. Cl.⁶ ................................................. G01N 21/41
[52] U.S. Cl. ............................. 356/136; 359/509; 134/8
[58] Field of Search ........................... 356/246, 128–137, 356/244, 440, 442; 250/576, 573, 574, 900–907; 359/507, 509, 512, 514; 134/4, 6, 8, 22.1, 22.11; 15/246

[56] References Cited

U.S. PATENT DOCUMENTS

| | | | |
|---|---|---|---|
| 3,072,503 | 1/1963 | Baum | 134/8 |
| 3,564,262 | 2/1971 | Hach | 356/135 |
| 3,573,985 | 4/1971 | Schultz | 134/8 |
| 3,628,867 | 12/1971 | Brady | 356/136 |
| 3,819,513 | 6/1974 | Ishii et al. | 210/23 |
| 3,883,431 | 5/1975 | Ishii et al. | 210/134 |
| 4,165,179 | 8/1979 | Sato | 359/507 |
| 4,245,914 | 1/1981 | Clack | 356/440 |
| 4,336,074 | 6/1982 | Dinkelacker | 134/8 |
| 4,451,152 | 5/1984 | Topol et al. | 356/440 |
| 4,606,866 | 8/1986 | McGlothlin et al. | 359/507 |
| 4,895,602 | 1/1990 | Sagawa | 134/8 |
| 4,962,746 | 10/1990 | Miyata et al. | 356/128 |
| 5,015,091 | 5/1991 | Suzuki et al. | 356/135 |

FOREIGN PATENT DOCUMENTS

| | | |
|---|---|---|
| 0095858 | 7/1980 | Japan ................................. 359/509 |
| 62-232538 | 10/1987 | Japan . |
| 62-276438 | 12/1987 | Japan . |
| 6410152 | 1/1989 | Japan . |

Primary Examiner—Hoa Q. Pham
Attorney, Agent, or Firm—Cushman, Darby & Cushman

[57] ABSTRACT

In an apparatus for detecting a property of a liquid, light is emitted from a light emitting element towards an interface between a liquid to be measured and a prism in an interface channel. Reflected light from the interface is received by a light receiving device, and a refractive index of the liquid is obtained from the total reflection critical angle. A cleaning member capable of contacting the interface by the flow of the liquid is provided. The cleaning member may be a small body or a floating member, a tape/string member having one end fixed to a channel wall, or a wiper swingable by the flow of the liquid.

7 Claims, 14 Drawing Sheets

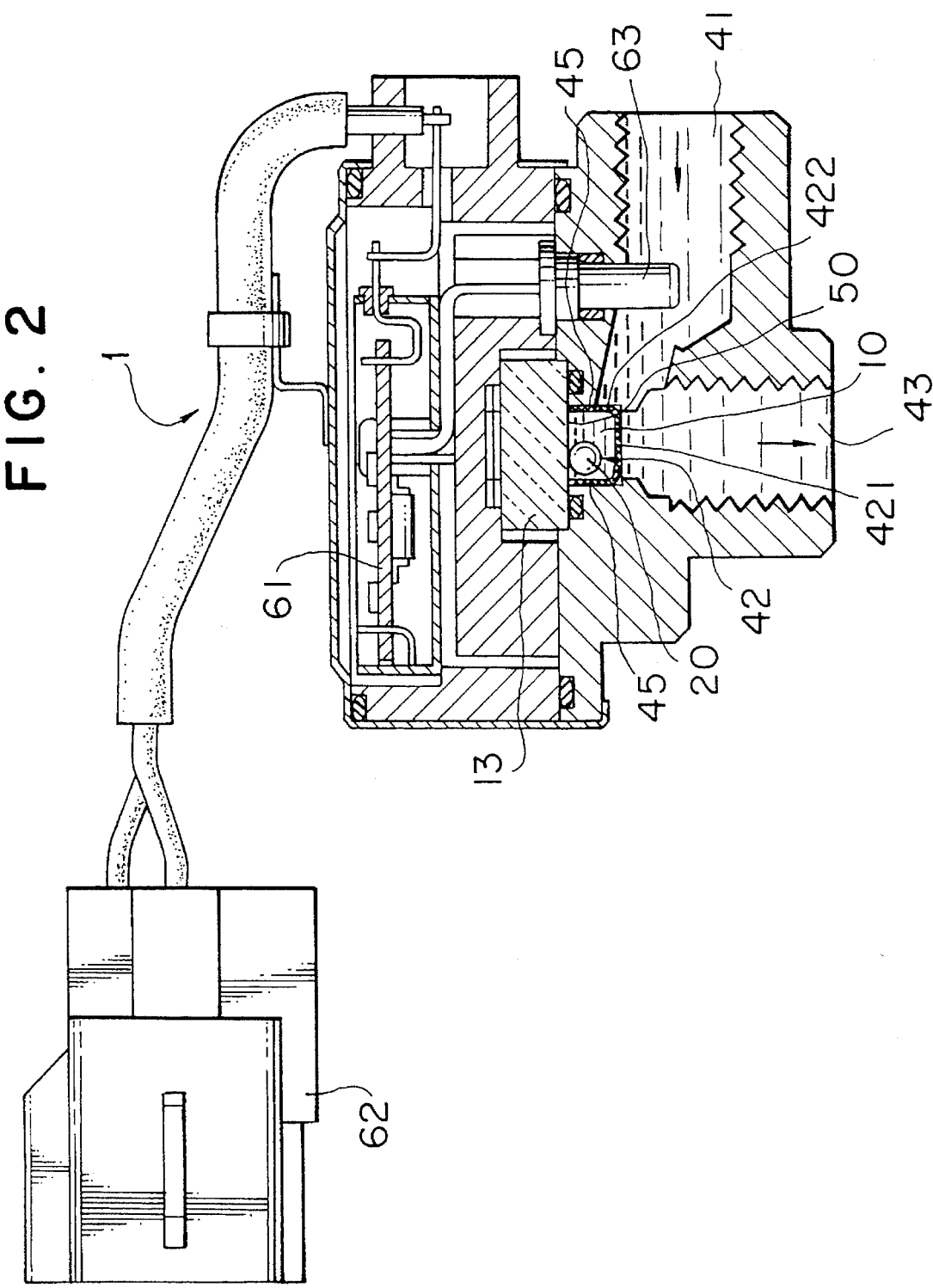

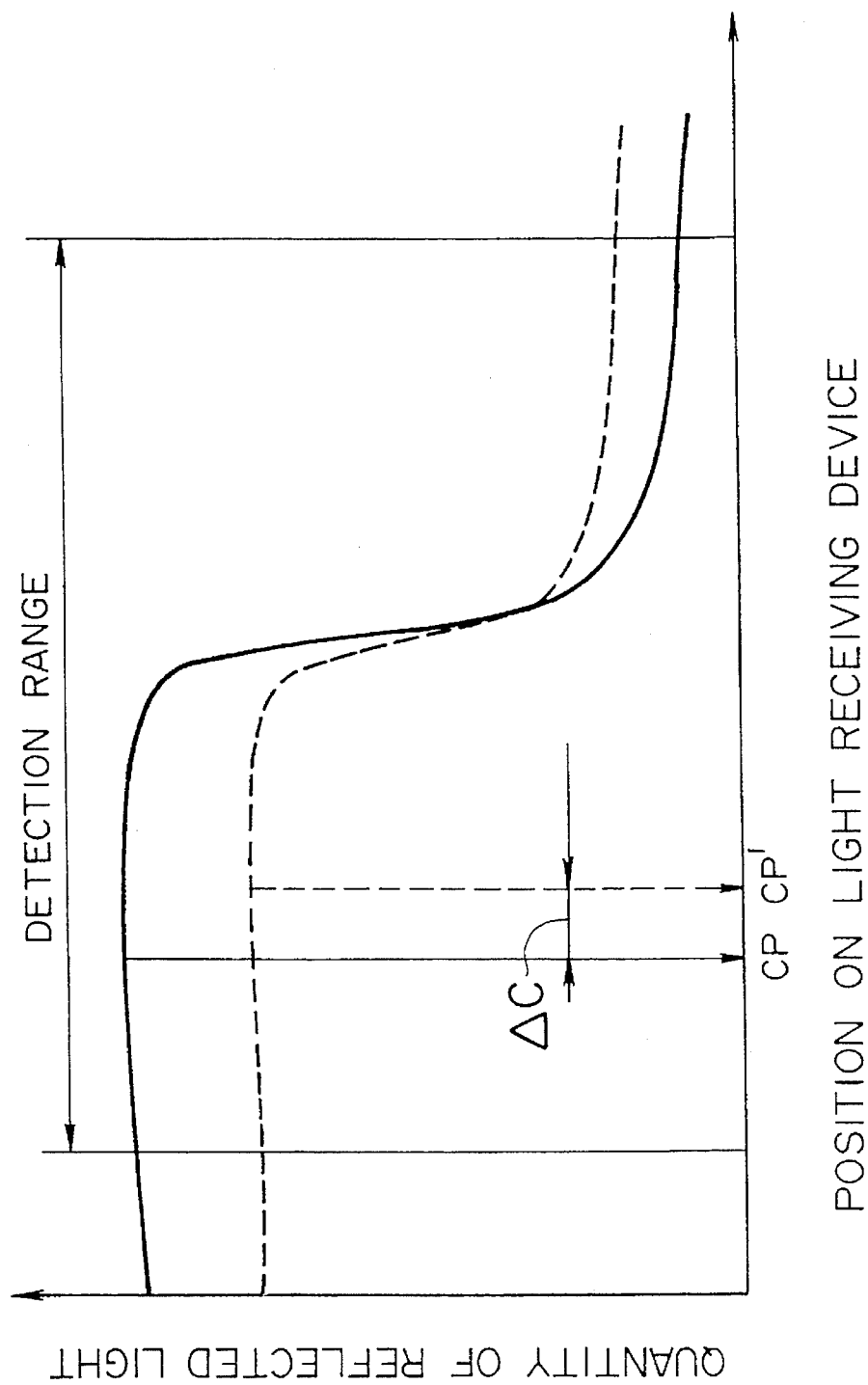

APPARATUS FOR DETECTING A PROPERTY OF A LIQUID

This is a continuation of application Ser. No. 08/120,378, filed on Sep. 14, 1993 now abandoned.

BACKGROUND OF THE INVENTION

1. Field of the Invention

This invention relates to an apparatus for optically detecting a property of a liquid. For example, this invention is applicable to an apparatus for detecting a density of methanol or a property of gasoline in a motor vehicle fuel.

2. Description of Related Art

In recent years, its has been proposed to mix an extraneous component such as methanol or ethanol with gasoline so as to realize a cleaner exhaust.

To detect a density of the extraneous component, optical liquid property detectors utilizing the refractive index of light have been proposed (for example, in Japanese Patent Unexamined Publication Nos. 62-216438, 62-232538, and 64-10152). Such optical detectors can be used to detect a volatility of gasoline to determine whether the gasoline is heavy or light.

This kind of liquid property detector is arranged to detect the light reflected in an interface between a prism and a liquid to be measured. However, a contaminative material is contained in the liquid, although its amount is small. If such a material attaches to the interface, the incident light is scattered, resulting a measurement error. For example, in case that the liquid to be measured is gasoline, high-boiling point materials (oxides, materials caused by deterioration) of gasoline, inorganic materials such as Mn, S, Zn, and Cu, and ester or glycolic materials from a sealing agent on a piping or other members attach to the interface. As a result, such contamination deviates a quantity of reflected light on a light receiving element from a true value. Accordingly, a centroidal position of the reflected light is changed to cause a detection error.

SUMMARY OF THE INVENTION

In view of the above-described problem, an object of the present invention is to provide a liquid property detection apparatus capable of preventing or removing a contamination on an interface between a light emitting portion and a liquid to be measured, and having stable characteristics.

To this end, according to the present invention, there is provided an apparatus for detecting a property of a liquid, comprising a light emitting unit in contact with a liquid to be measured, for emitting inspection light towards an interface between the light emitting unit and the liquid, a light sensor for receiving light reflected at the interface, a unit for determining a property of the liquid by receiving an output signal from the light sensor and detecting a total reflection critical angle on the liquid, a chamber through which the liquid flows, and a cleaning member disposed in the chamber and capable of moving in contact with the interface on the light emitting unit along the flow of the liquid to wipe off material attached to the interface.

BRIEF DESCRIPTION OF THE DRAWINGS

FIG. 2 is a cross-sectional view taken along the lines II—II of FIG. 1;

FIG. 19 is a graph showing a change in the quantity of received light due to the existence of contamination.

DESCRIPTION OF THE PREFERRED EMBODIMENTS

Figure 1:
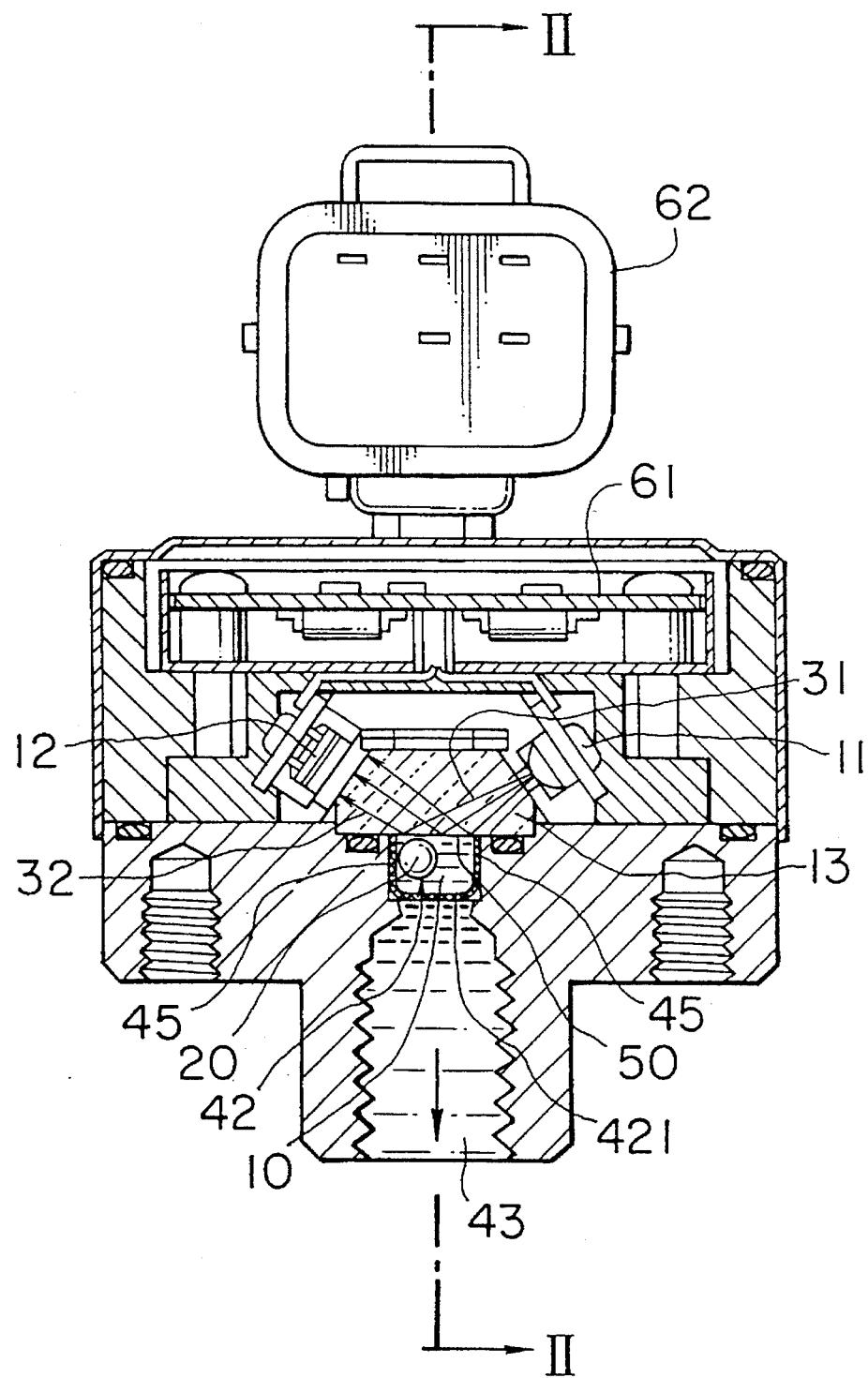
FIG. 1 is a cross-sectional view of a liquid property detection apparatus in accordance with a first embodiment.

Referring to FIGS. 1 and 2, in a liquid property detection apparatus 1 in accordance with a first embodiment of the present invention, light 31 is emitted from a light emitting element 11 in a light emitting unit towards an interface 50 between a liquid 10 to be measured which flows through an interface channel 42 and a prism 13 having a known refractive index $n_1$. Reflected light 32 from the interface 50 is received by a light receiving device 12 of a light sensor, and then a refractive index $n_2$ of the liquid 10 is obtained from the total reflection critical angle. A small solid body 20 is disposed in the channel 42 as a floating member capable of contacting the interface 50 on the prism 13 by a flow of the liquid.

The liquid 10 is gasoline. As shown in FIG. 2, the liquid 10 is caused to flow into the interface channel 42 through an inflow pipe 41 and to flow out of the interface channel 42 through an outflow pipe 43.

The liquid 10 contacts the prism 13 in the interface channel 42 at the interface 50. The inflow pipe 41 and the outflow pipe 43 are arranged so that the axes thereof intersect each other approximately at right angles.

The light receiving device 12 and the light emitting element 11 are mounted on the opposite sides of the prism 13. Reflected light 32 totally reflected by the interface 50 in the light 31 emitted from the light emitting element 11 towards the prism 13 reaches the light receiving device 12.

Figure 15:
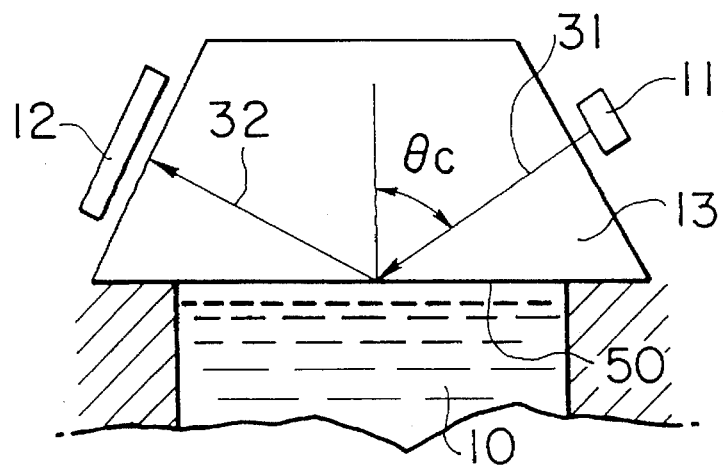
FIG. 15 is an enlarged cross-sectional view of a prism portion of a detection apparatus.

That is, as shown in FIG. 15, the light 31 is incident upon the interface 50 between the prism 13 and the liquid 10, and the reflected light 32 is measured to calculate the total reflection critical angle $\theta_c$, thereby obtaining the refractive index $n_2$ of the liquid 10.

Figure 16:
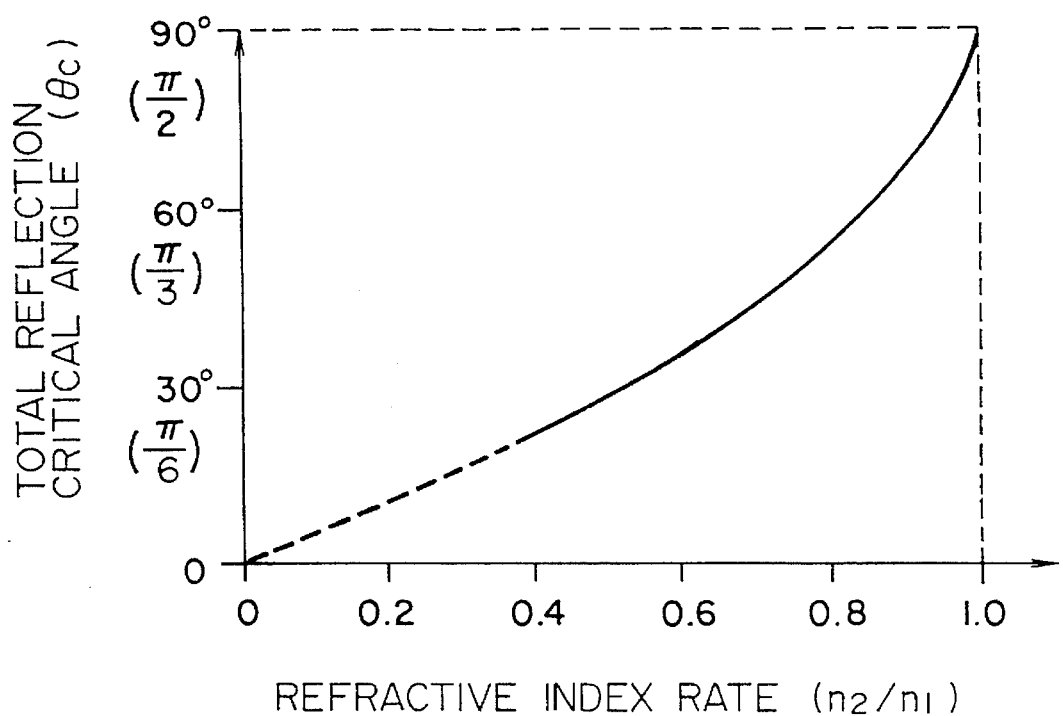
FIG. 16 is a graph showing the relationship between the refractive index and the total reflection critical angle.

Ordinarily, the interface 50 is a flat surface. If the refractive index of the prism 13 is $n_1$, a relational equation $\sin\theta_c = n_2/n_1$ is established. The relationship between the refractive index rate and the total reflection critical angle is indicated by a nonlinear curve as shown in FIG. 16.

Figure 17:
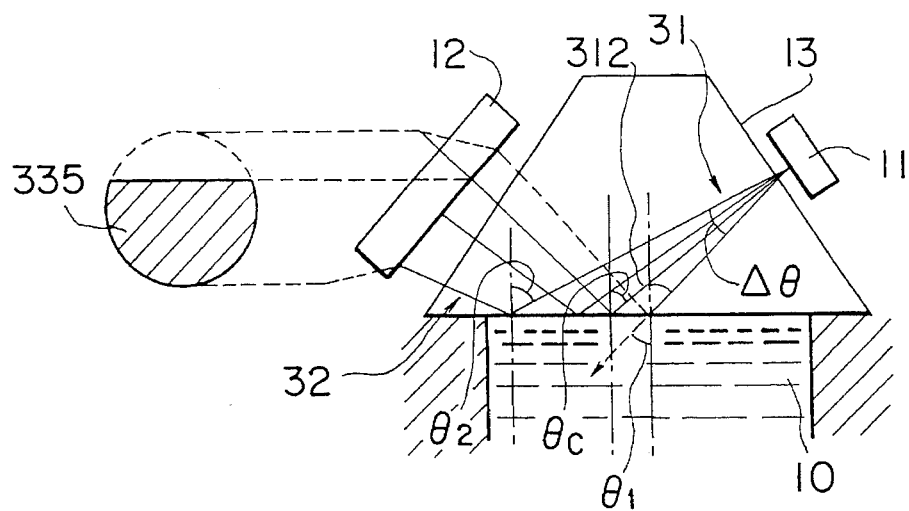
FIG. 17 is a diagram of an optical system.

In FIG. 15, the incident light 31 is represented by a straight line. Ordinarily, however, it is a beam having a certain divergence angle $\Delta\theta$ as shown in FIG. 17, and a cross-sectional shape of such a beam is generally circular. In such a case, reflected light 32 reaching the light receiving device 12 has a sectional shape as represented by a partial circle 335 shown at the left hand side of FIG. 17. The hatched portion represents a section of the refracted light.

If the refractive index $n_2$ of the liquid 10 is changed and then the total reflection critical angle $\theta_c$ is changed accordingly, the sectional shape of reflected light 32 is changed as indicated in FIGS. 18A to 18D. The hatched portions represent sections of the reflected light. If $\theta_c$ is small, the incident light is entirely reflected to form a whole circular cross-sectional shape shown in FIG. 18A. If $\theta_c$ is large, the incident light is not reflected, and then no reflected light is obtained as of $\theta_c$, a partial circle such as that shown in FIG. 18B or shown in FIG. 18D. With respect to an intermediate value 18C is obtained. The broken line in FIGS. 18B to 18D indicates the existence of very weak reflected light.

Figures 18A, 18B, 18C, 18D:
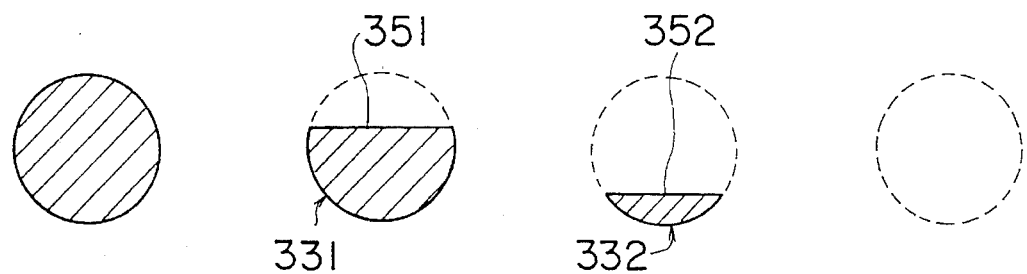
FIGS. 18A to 18D are cross-sectional views of reflected light.

That is, when the incident angle $\theta$ of incident 17, and when the total reflection critical angle $\theta_c$ is light 31 is within the range of $\theta_1$ and $\theta_2$ as shown in FIG. 17, and when the total reflection critical angle $\theta_c$ is equal to or smaller than $\theta_1$, incident light 31 is entirely sectional shape shown in FIG. 18A. When $\theta_c$ is equal to or reflected and reflected light 32 forms a whole-circle larger than 92, reflected light 32 has a shape such as that shown in FIG. 18D representing a non-reflecting state. When $\theta_1 < \theta_c < \theta_2$, reflected light 32 has the shape of a partial circle such as that shown in FIG. 18B or 18C.

The light receiving device 12 detects a centroidal position (CP) on the sectional shape of reflected light 32 and converts it into a corresponding electrical signal. The refractive index $n_2$ of the liquid is calculated by a determination section 61 (FIGS. 1 and 2) from the magnitude of the corresponding electrical signal. An incident angle of an incident light 312 corresponding to a chord 351 or 352 of the partial circle 331 or 332 is the total reflection critical angle $\theta_c$.

If contamination is attached to the interface 50, the quantity of reflected light received on the light receiving device is changed from a state indicated by the solid line (no contamination) to a state indicated by the broken line. The true centroidal position (CP) of reflected light 32 is thereby shifted to a centroidal position (CP') by $\Delta C$, and the true centroidal position cannot be detected.

The prism 13 is formed of glass (refractive index $n_1=1.7$).

A plurality of small bodies 20 are disposed in the interface channel 42. Only one body 20 is shown. A member 45 formed of a wire network is provided for preventing the bodies 20 from being carried away in the interface channel 42 so as to cover an inlet portion 421 and an outlet portion 422 (FIG. 2) through which the liquid 10 is introduced and discharged. The carry-away prevention member 45 has a basket-like shape. Meshes of the carry-away prevention member 45 are finer than the dimension of the small bodies 20.

If the particle size of the small bodies 20 is smaller than the meshes of the carry-away prevention member 45, the small bodies 20 can be carried away into the flow passage. The particle size of the small bodies 20 is selected so as to be greater than the mesh size of the carry-away prevention member 45 and so that the problem of a contamination removable area being smaller than a required detection area can be avoided.

On the other hand, the mesh size of the carry-away prevention member 45 is determined by a required value of pressure loss.

Under these conditions, it is preferable that the small bodies 20 have a volume of 50% or less of the volume of the interface channel 42.

Figure 3A:
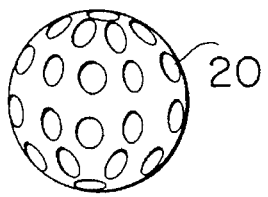
FIGS. 3A to 3E show modifications of small bodies of the first embodiment, respectively.
Figure 3B:
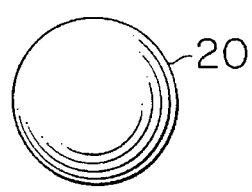
Figure 3C:
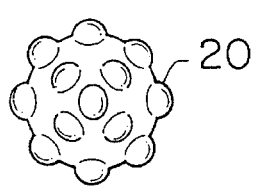
Figure 3D:
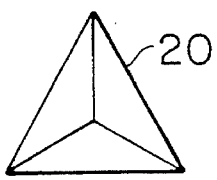
Figure 3E:
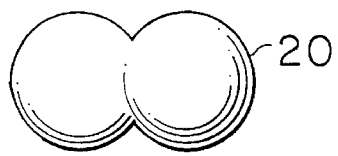

The small bodies 20 are formed of a fluorocarbon polymer containing carbon fibers such that they do not damage the prism while its durability in the liquid 10 is sufficiently high. The small bodies 20 may have the shape of a sphere with small spherical recesses (FIG. 3A), a sphere (FIG. 3B), a sphere with small spherical projections (FIG. 3C), a regular tetrahedron (FIG. 3D), a combination of two spheres (FIG. 3E) or the like.

The shape and the specific gravity of the small bodies 20 are selected so that the small bodies can move easily along the flow of the liquid.

As the material of the small bodies 20, a fluorocarbon rubber, glass, a ceramic, a metal or the like can be used as well as a fluorocarbon polymer. The small bodies may be formed as hollow members to have a suitable specific gravity.

Also, it is preferable to use a material having a small reflectivity to form the surface of the small bodies 20.

To satisfy these conditions, a central portion and a surface portion may be formed of different materials. For example, the small body may be a polytetrafluoroethylene ball having an iron core coated with polytetrafluoroethylene, or a fluorocarbon rubber ball having an iron core coated with a fluorocarbon rubber.

A component indicated by 62 in FIGS. 1 and 2 is a connector, and a component indicated by 63 in FIG. 2 is a temperature compensation thermistor.

The operation of this embodiment will be described below.

Figure 4A:
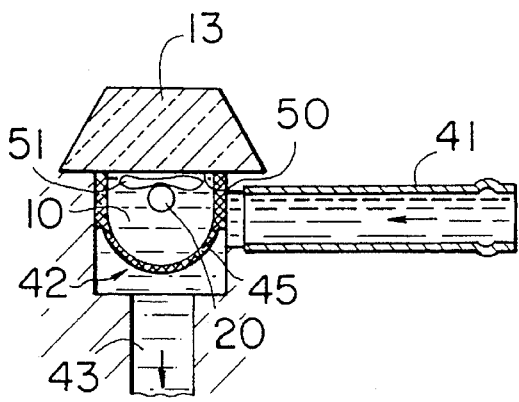
FIGS. 4A and 4B are cross-sectional views of a prism portion of the apparatus shown FIG. 1.
Figure 4B:
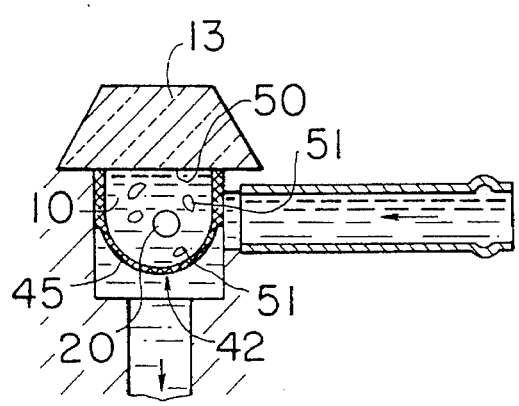

When the small bodies 20 contact contamination 51 attached to the interface 50 between the prism 13 and the test object liquid 10 (FIG. 4A), a separating force is applied to an intermolecular attraction force acting between the molecules of the contamination 51 so that the contamination 51 is reduced into particles and separated (FIG. 4B).

That is, the contamination 51 is ordinarily caused to be attached to the interface 50 by an intermolecular attraction force. Therefore, the application of a physical external force to the contamination 51 by the small bodies 20 is effective in removing the contamination 51.

The liquid 10 flows in one direction as indicated by the arrows in FIGS. 4A and 4B, while the small bodies 20 are enclosed in the interface channel 42 by the carry-away prevention member 45. Therefore, the small bodies 20 move while floating in the interface channel 42 by receiving the force of the liquid 10. By this movement, the solid bodies 20 collide against the interface 50 between the prism 13 and the liquid 10 to reduce the contamination 51 into pieces, thereby separating the contamination 51 from the interface 50.

The small bodies 20 are also effective in preventing contamination 51 from growing.

Figure 5:
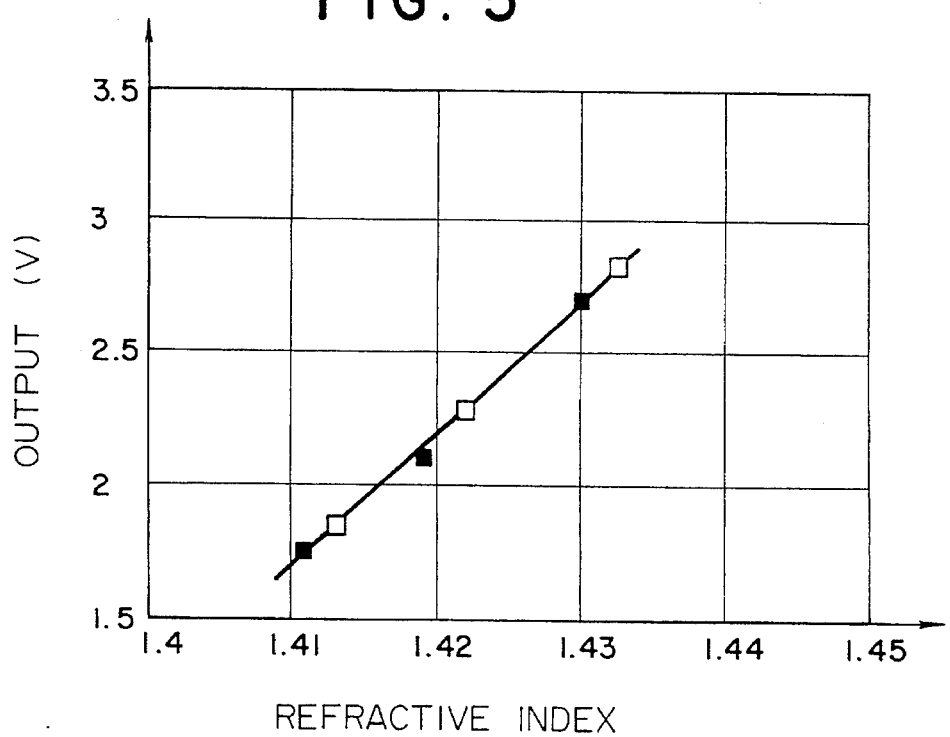
FIG. 5 is a graph of a change with respect to time in an output of the first embodiment.

In the situation where the small bodies are enclosed, the initial values (■) of the output voltage of he light receiving device 12 with respect to the refractive index $n_2$ and the values (□) of the output voltage measured after 100 hours operation are as indicated on one straight line in FIG. 5, and substantially no difference is observed between the outputs in the initial state and the 100 hours operation state.

Figure 6:
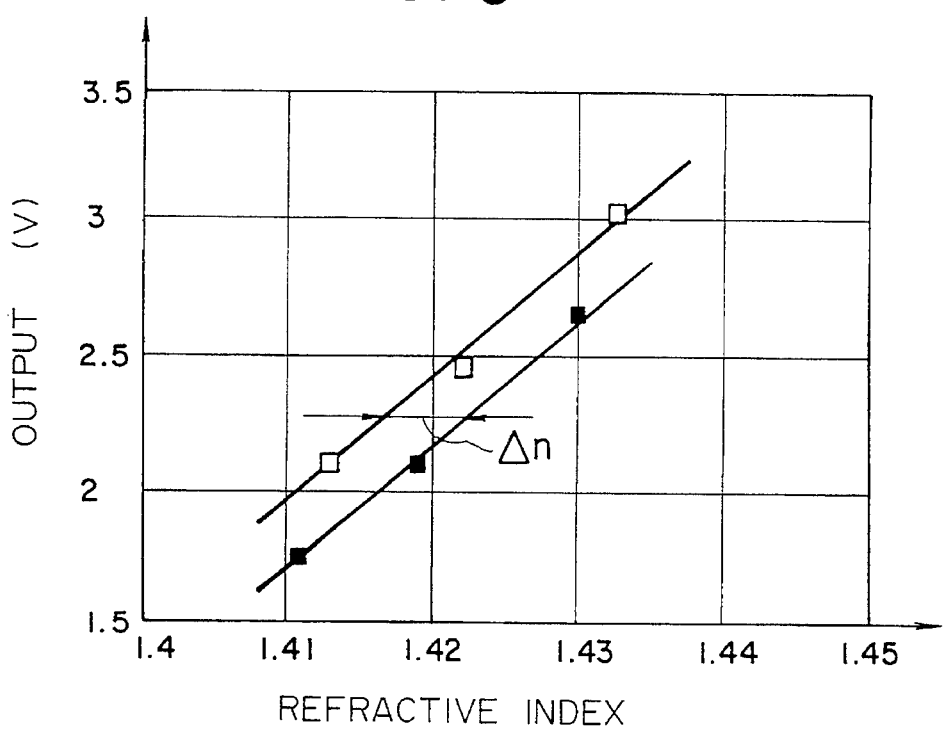
FIG. 6 is a graph of a change with respect to time in an output of a conventional liquid property detection apparatus.

On the other hand, in a conventional liquid property detection apparatus having no small bodies. The output voltage values (□) after 100 hours operation are greater than initial output voltage values (■), as shown in FIG. 6. The refractive index is calculated excessively ($\Delta n=12\%$), resulting in a measurement error.

The data shown in FIG. 5 is obtained by an experiment wherein three iron balls each having a diameter of 3 mm are enclosed as small bodies in the interface channel 42.

Thus, a liquid property detection apparatus capable of preventing or removing a contamination on the interface 50 between the prism 13 and the liquid can be provided by the application of the simple structure in accordance with the embodiment described above.

If the flowability of the liquid 10 in the interface channel is improved by a means for causing intermittent impulsive flows or the like of the liquid, the effect of preventing or removing a contamination is further improved.

The positions of the outflow pipe 43 and the inflow pipe 41 are not limited to those in the above-described embodiment. The liquid 10 may flow reversely, and the inflow pipe 41 and the outflow pipe 43 may be set at any angle.

In the above-described embodiment, glass of $n_1=1.7$ is used for the prism 13. However, the prism 13 may be made of any other transparent material, e.g., acrylic ($n_1=1.49$), polycarbonate ($n_1=1.58$), or polyimide ($n_1=1.62$ to $1.66$).

FIGS. 7A to 7D show examples of modifications of the above-described embodiment in which the carry-out prevention member is changed.

Figure 7A:
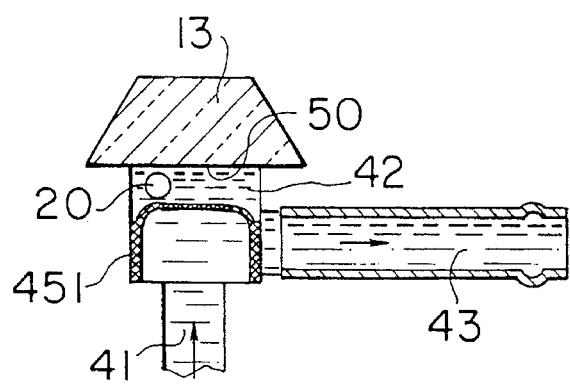
FIGS. 7A to 7D are cross-sectional views of modifications of the prism portion.

FIG. 7A shows an arrangement in which a basket-like carry-out prevention member 451 is inverted in the interface channel 42. The space in which small bodies 20 move can be thereby limited to a narrower space in the interface channel 42 in the vicinity of the interface 50.

Figure 7B:
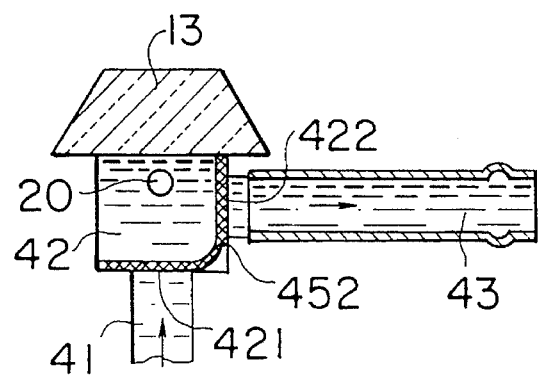

FIG. 7B shows an arrangement in which a carryout prevention member 452 having two flat surfaces intersecting each other so as to form an L-like shape. The carry-out prevention member 452 is attached so that the two surfaces forming the L-like shape cover the inlet 421 and the outlet 422 of the interface channel 42, respectively.

Figure 7C:
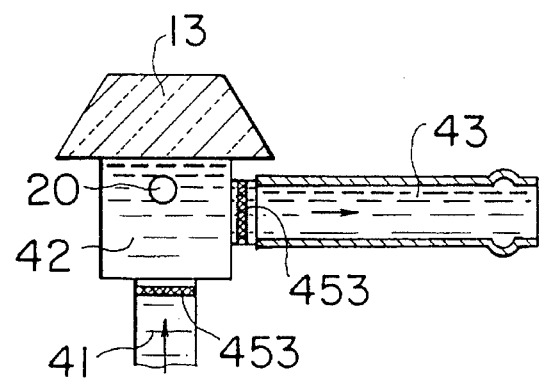

FIG. 7C shows an arrangement in which two flat carry-out prevention members 453 are attached to portions of the inflow pipe 41 and the outflow pipe 42 in the vicinity of the interface channel 42, respectively.

Figure 7D:
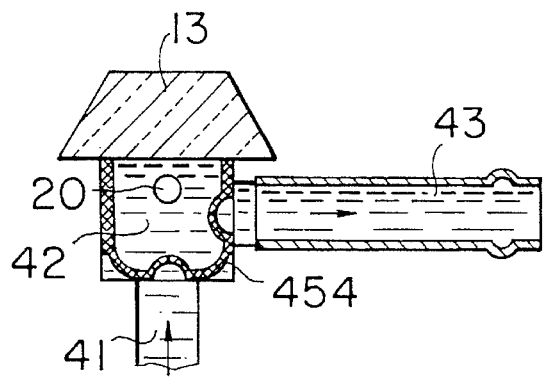

FIG. 7D shows an arrangement in which a carry-out prevention member 454 has an uneveness in its surface such that small bodies 20 can move actively.

FIGS. 8A to 8D show examples of other modifications of the above-described embodiment in which the shape of the passage through which the liquid flows is changed.

Figure 8A:
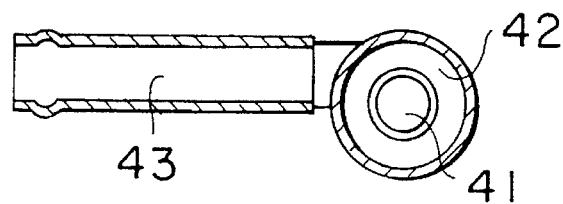
FIGS. 8A to 8D are cross-sectional views of modifications of the liquid flow passage.

FIG. 8A shows an arrangement in which the inflow pipe 41 and the outflow pipe 43 are disposed so as to be perpendicular to each other, their axes do not meet each other.

Figure 8B:
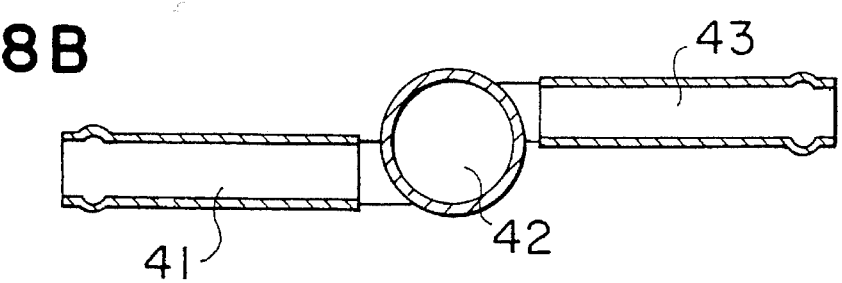

FIG. 8B shows an arrangement in which the inflow pipe 41 and the outflow pipe 43 are disposed parallel to each other with a horizontal certain offset between their axes.

Figure 8C:
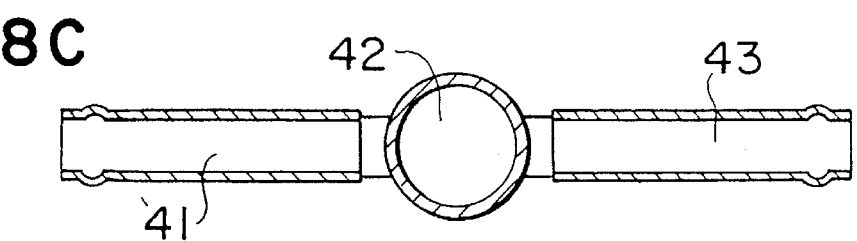

FIG. 8C shows an arrangement in which the inflow pipe 41 and the outflow pipe 43 are disposed on the same axial line without an offset.

Figure 8D:
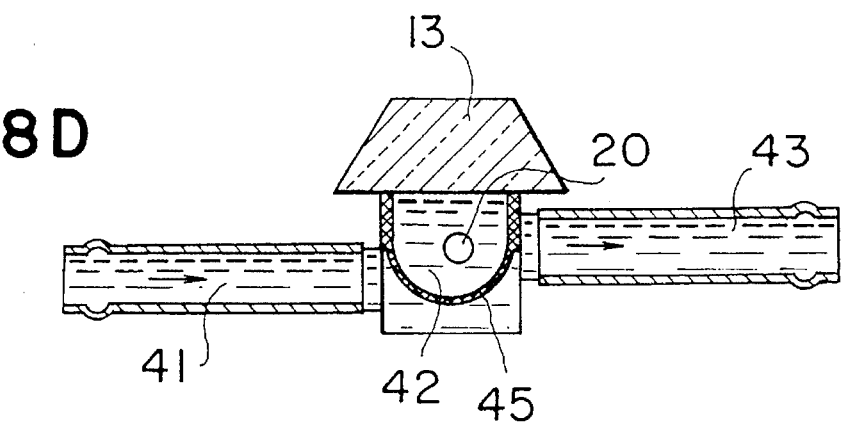

FIG. 8D shows an arrangement in which the inflow pipe 41 and the outflow pipe 43 are disposed parallel to each other with a vertical certain offset between their axes.

Figure 9:
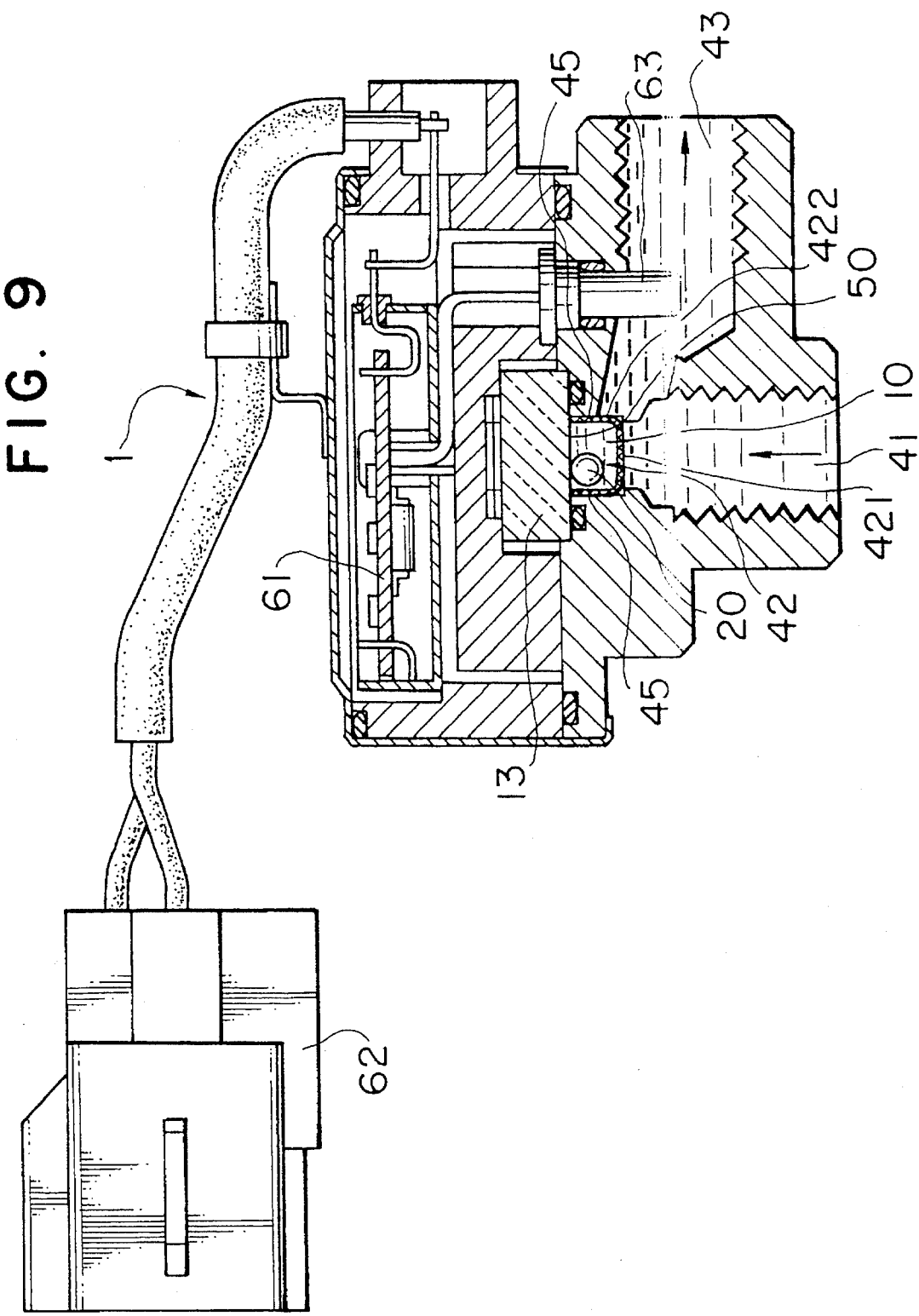
FIG. 9 is a cross-sectional view of a liquid property detection apparatus in accordance with a second embodiment of the present invention.

FIG. 9 shows a second embodiment of the present invention having the inflow pipe 41 and the outflow pipe 43 of the first embodiment interchanged with each other.

In this embodiment, small bodies 20 have spherical shape, a volume of 10 to 30% of the capacity of the interface channel 42, and a specific gravity of 1 to 3.

Preferably, the liquid property detection apparatus 1 is attached to a fuel system of a motor vehicle so that the outflow pipe 43 extends horizontally, whereby small bodies 20 can move smoothly.

Figure 10:
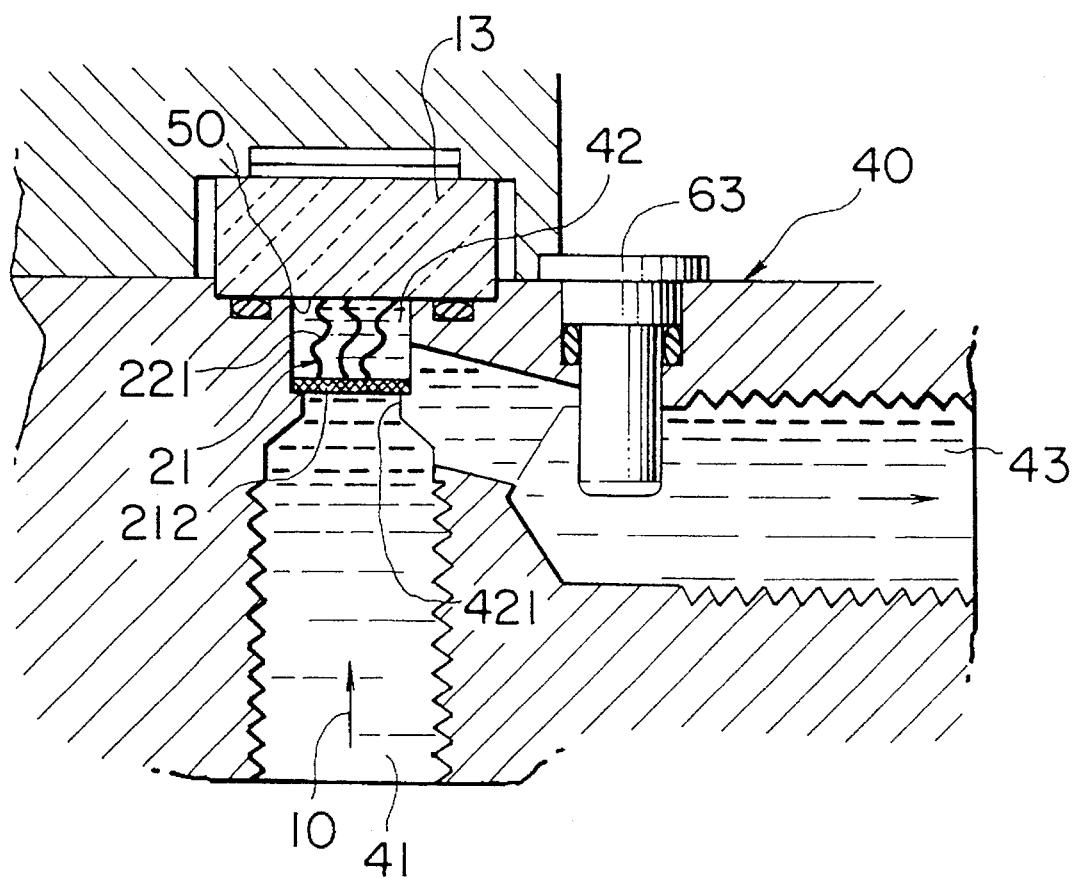
FIG. 10 is an enlarged cross-sectional view of a portion in the vicinity of an interface channel in accordance with a third embodiment of the present invention.

FIG. 10 shows a third embodiment of the present invention using a fixed cleaning member 21 including soft tape/string member 211 swaying in the liquid. The fixed cleaning member 21 is fixed in an interface channel 42 in a housing 40 by an attachment plate 212. The tape/string member 211 can sway along the flow of the liquid 10.

The tape/string member 211 is caused to move in contact with the interface 50 to wipe off a deposit on the interface 50.

The attachment plate 212 is disposed on an inlet portion 421 so as to extend in a direction perpendicular to the flow of the liquid 10. The attachment plate 212 is formed of a network member such that the pressure loss caused by the attachment plate 212 is small and the flow of the liquid 10 is not impeded.

If cape/string member is formed by a tape, a width thereof is changed according to the width of the inlet of the interface channel 42. For example, the width of the inlet is about 6 mm, the tape width is 2 mm or larger.

Preferably, the length of the tape-like member 211 is larger than a gap between the interface 50 and the attachment plate 212 and is not larger than 1.5 times the gap.

A number of tape-like members can be used as a tape/string member 211 in case that the length of the interface 50 is long.

As the material of the tape/string member 211, a material having improved resistance to gasoline, e.g., a fluoro rubber, a fluorocarbon resin, polyethylene, nylon, polyimide, polyacetal, polytetrafluoroethylene, phenol, or the like, may be used.

Preferably, the material of the tape/string member 211 has a small reflectivity such that the intensity of reflected light is not substantially changed.

The tape/string member 211 may be formed of cords, strings, or a network as well as a tape.

Figure 11A:
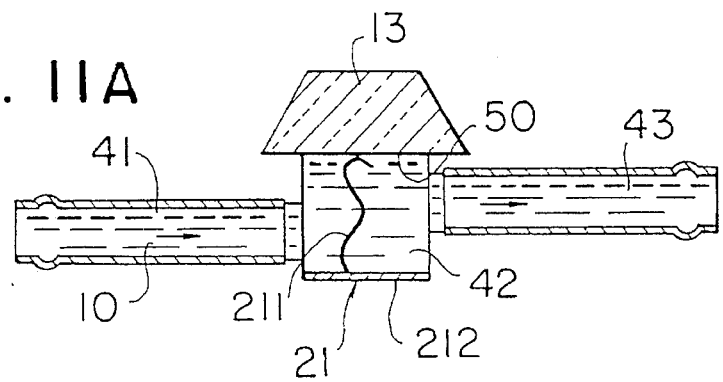
FIGS. 11A to 11d are enlarged cross-sectional views of modifications of the arrangement shown in FIG. 10.
Figure 11B:
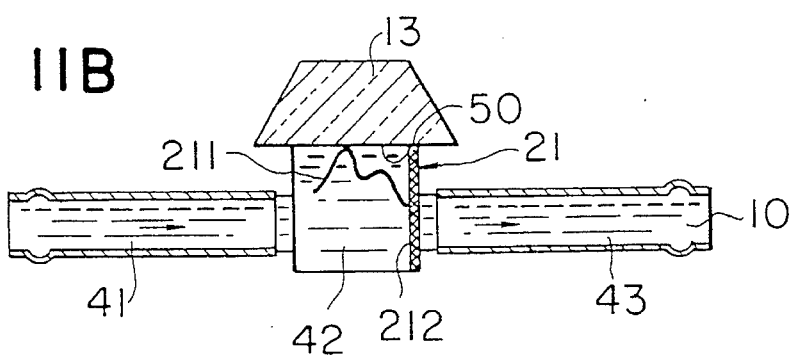
Figure 11C:
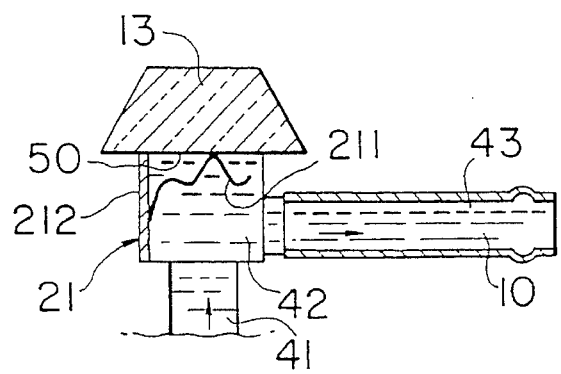

The attachment plate 212 may be attached parallel to the direction of the flow of the liquid 10 as shown in FIG. 11A or 11C.

Figure 11D:
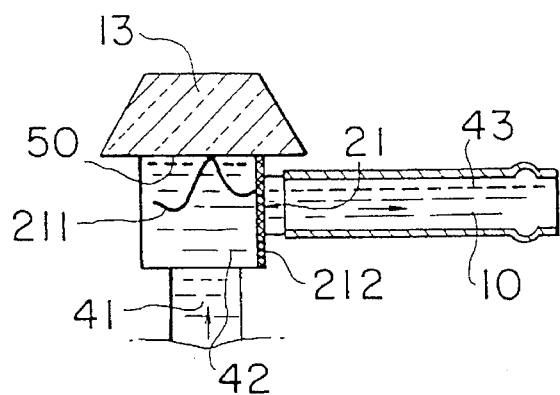

Also, the attachment plate 212 may be provided on the outflow side of the liquid 10, as shown in FIG. 11B or 11D.

Figure 12:
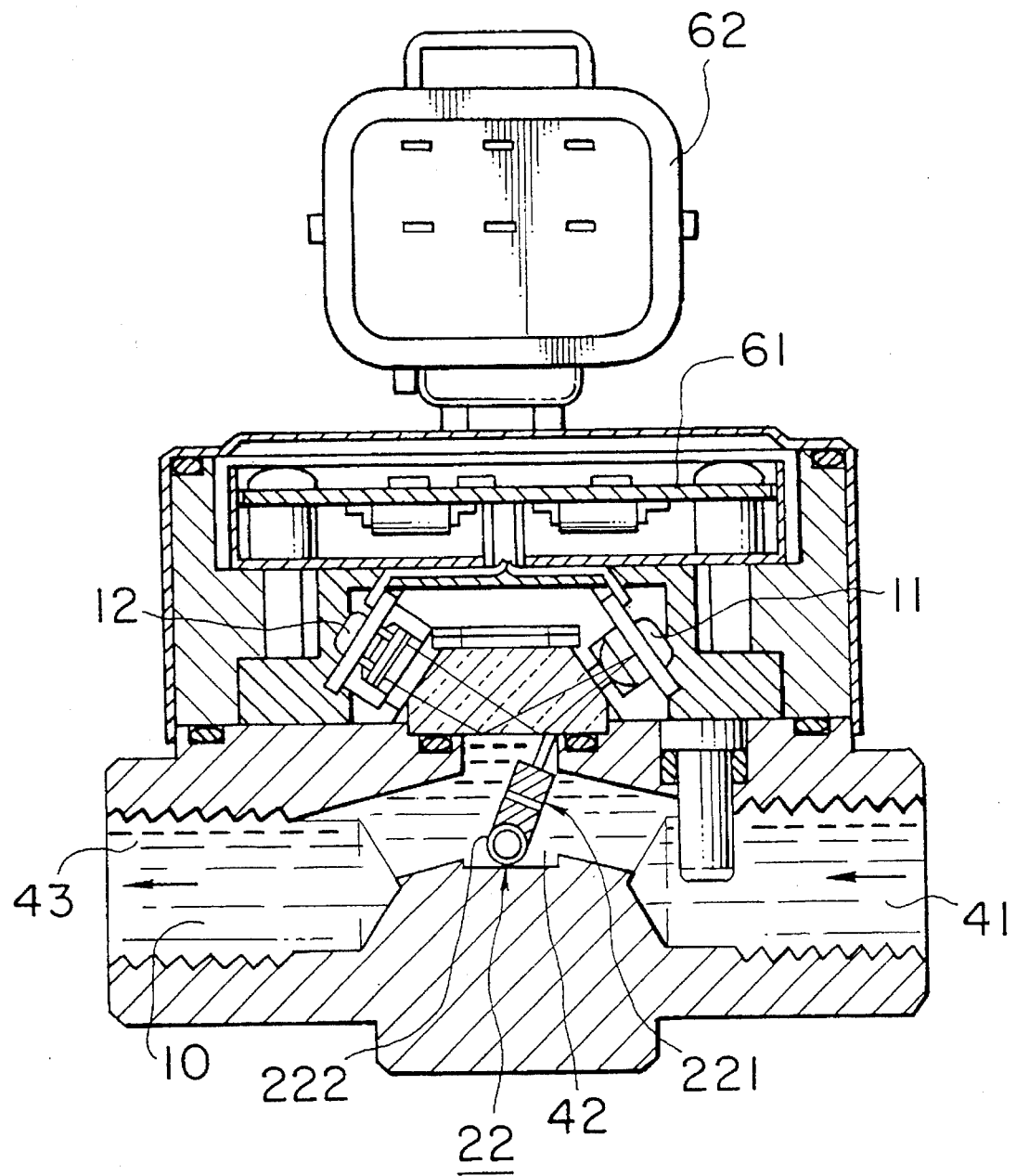
FIG. 12 is a cross-sectional view of a liquid property detection apparatus in accordance with a fourth embodiment of the present invention.

FIG. 12 shows a fourth embodiment in which an inflow pipe 41 and an outflow pipe 43 for introducing and discharging a liquid 10 are formed parallel to one plane, and in which a fixed cleaning member 22 is formed of a wiper 221 and a resilient member 222.

The liquid 10 flows from the inflow pipe 41 to the outflow pipe 43 in a housing 40.

Figure 13:
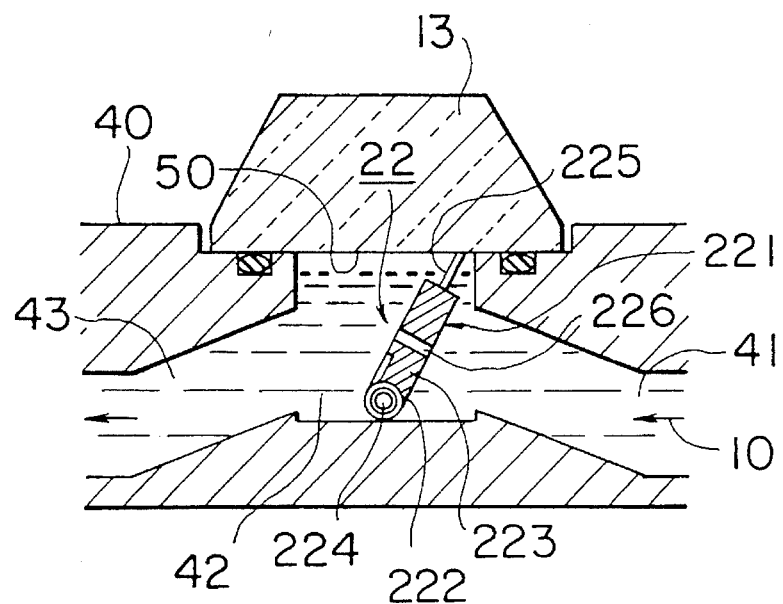
FIGS. 13 and 14 are enlarged cross-sectional views of a portion around the cleaning member of the embodiment shown in FIG. 12.

As shown in FIG. 13, the fixed cleaning member 22 has a wiper 221 for wiping the interface 50 and a return spring, i.e., the resilient member 222 for urging the wiper 221 in a direction opposite to the flow direction of the liquid 10, i.e., the direction toward the inflow pipe 41.

The wiper 221 has an arm 223, a pivot portion 224 for pivotally supporting the arm 223 on the housing 40 so that the arm 223 is swingable in the direction of the flow of the liquid 10, and a sweeper 225 attached to the arm 223, linked to the swinging of the arm 223 and slidable on the interface 50.

The arm 223 and the sweeper 225 have a fluid resistance against the flow of the liquid 10.

The arm 223 of the wiper 221 is swingable on the pivot portion 224 in the direction in which the fluid 10 flows.

The soft sweeper 225 is attached to the end of the arm 223 opposite to the pivot portion 224. The sweeper 225 slides on the interface 50 as the arm 223 swings.

The arm 223 is disposed across the interface channel 42 so as to substantially close the channel 42, but a communication hole 226 through which the liquid 10 can flow is formed in a central portion of the arm 223.

The arm 223 is urged by the resilient member 222 to be inclined to close the outlet opening of the inflow pipe 41, as shown in FIG. 13, if the flow of the liquid 10 is very weak or the liquid 10 stagnates.

Figure 14:
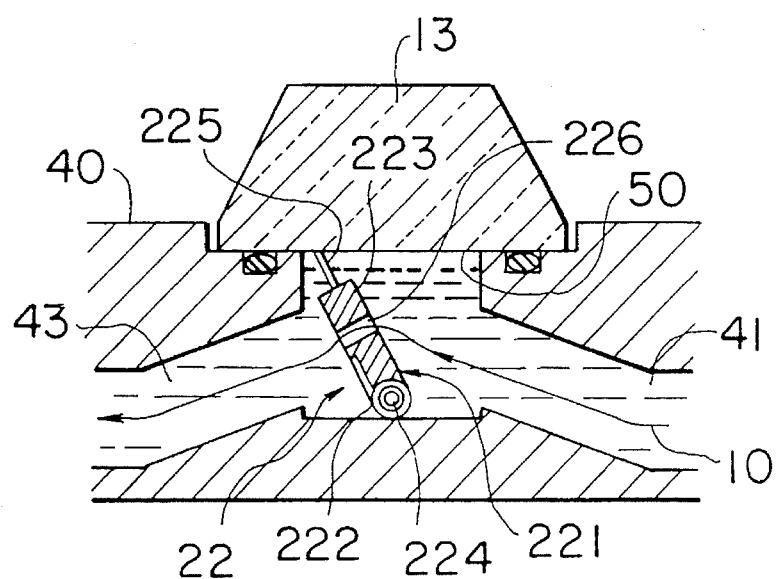

However, when the liquid 10 flows smoothly, a torque occurs by the fluid resistance of the arm 223 and finally prevails over the urging force of the resilient member 222 to incline the arm 223 toward the outflow pipe 43, as shown in FIG. 14.

If the flow of the liquid 10 becomes weak again, the wiper 221 is restored to the original state (FIG. 13).

As described above, the wiper 221 can move reciprocatively on the interface 50 to wipe off a deposit on the interface 50.

A rubber resistant to the liquid 10 is used as the material of the sweeper 225. For example, nitrile rubber, fluoro rubber or the like is used.

Preferably, the color of the sweeper 225 is made black to prevent reflection of incident light 31.

The arm 223 of the wiper 221 is formed of a material resistant to the liquid 10. For example, if the liquid is gasoline, an aluminum, an iron, a copper metal, phenol, polyphenylenesulfide, diarylphthalate, or the like is used.

The return spring provided as the resilient member 222 has the shape of a coil spring and is formed of a piano wire (SWPA), a spring stainless steel (SUP) or the like. If the liquid 10 contains water, stainless steel is preferred instead of piano wire.

What is claimed is:

1. An apparatus for detecting a property of a liquid, comprising:

a unit in contact with a liquid to be measured, said unit emitting inspection light towards an interface between the light emitting unit and the liquid;

a sensor for receiving light reflected at the interface;

a unit for determining a property of the liquid by receiving an output signal from said light sensor;

an accommodation chamber through which the liquid flows; and a cleaning member disposed in said accommodation chamber and including a freely movable part in contact with said interface on said light emitting unit moving in response to the flow of the liquid to wipe off a deposit on said interface, and wherein said cleaning member comprises a floating member which floats by the flow of the liquid, said cleaning member having a dimension which completely occupies neither a lateral cross-section of said accommodation chamber, nor a longitudinal cross-section of said accommodation chamber, so that said cleaning member can move freely in said accommodation chamber to collide against said interface on said light emitting unit in response to the flow of the liquid in said accommodation chamber.

2. An apparatus according to claim 1, wherein said determining unit detects a total reflection critical angle on the liquid.

3. An apparatus according to claim 1, wherein a carry-away prevention member which allows passage of the liquid but does not allow passage of said floating member is provided at an inflow portion and an outflow portion of said accommodation chamber.

4. An apparatus according to claim 1, wherein a surface of said floating member is formed of a material having a small reflectivity.

5. An apparatus detecting a property of a liquid, comprising:

a unit in contact with a liquid to be measured, said unit emitting inspection light towards an interface between the light emitting unit and the liquid;

a sensor for receiving light reflected at the interface;

a unit for determining a property of the liquid by receiving an output signal from said light sensor;

an accommodation chamber through which the liquid flows; and a cleaning member disposed in said accommodation chamber and including a freely movable part in contact with said interface on said light emitting unit moving in response to the flow of the liquid to wipe off a deposit on said interface, wherein said cleaning member has one end connected to said accommodation chamber.

6. An apparatus according to claim 5, wherein said cleaning member includes a soft tape/string member swayingly movable in the liquid.

7. An apparatus according to claim 5, wherein the liquid flows from the inflow port to the outflow port of said accommodation chamber, and said cleaning member has a wiper for wiping said interface on said light emitting unit, and a resilient member for urging said wiper in a direction opposite to the direction of the flow of the liquid, said wiper having an arm, a pivot portion for pivotally supporting said arm on said accommodation chamber so that said arm is swingable in the direction of the flow of the liquid, and a sweeper attached to said arm, linked to the swinging of said arm to slide on said interface on said light emitting unit, said arm and said sweeper having a fluid resistance to the flow of the liquid.

* * * * *